United States Patent [19]

Klier et al.

[11] 4,127,672
[45] Nov. 28, 1978

[54] INSECT REPELLANTS

[75] Inventors: Manfred Klier, Aumuhle; Udo Hoppe; Wolfgang Schritt, both of Hamburg, all of Germany

[73] Assignee: Beiersdorf Aktiengesellschaft, Hamburg, Germany

[21] Appl. No.: 768,222

[22] Filed: Feb. 14, 1977

Related U.S. Application Data

[63] Continuation of Ser. No. 398,272, Sep. 17, 1973, abandoned.

[30] Foreign Application Priority Data

Sep. 21, 1972 [DE] Fed. Rep. of Germany ....... 2246433

[51] Int. Cl.$^2$ .............................................. A01N 9/24
[52] U.S. Cl. .................................. 424/311; 260/465.4; 424/300; 424/304; 560/155; 560/157
[58] Field of Search ............... 424/311, DIG. 10, 300; 560/155

[56] References Cited

U.S. PATENT DOCUMENTS 3,594,171  7/1971  Kimura et al. ........................... 96/84

FOREIGN PATENT DOCUMENTS 721,081 12/1954 United Kingdom.

*Primary Examiner*—Leonard Schenkman
*Attorney, Agent, or Firm*—Bierman & Bierman

[57] ABSTRACT

Insect repellants having improved effectiveness, increased mucosa tolerance and compatibility with plastic objects containing, as an active ingredient, at least one 3-aminopropionic acid derivative which is disubstituted at the nitrogen atom, having the general structure

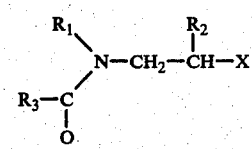

in which $R_1$ is a branched or unbranched alkyl radical having one to six carbon atoms, $R_2$ is hydrogen, methyl or ethyl, $R_3$ is a branched or unbranched alkyl or alkoxy group having one to eight carbon atoms, and X is —C≡N or —COOR$_4$, $R_4$ being a branched or unbranched alkyl group having one to six carbon atoms.

6 Claims, No Drawings

INSECT REPELLANTS

This is a continuation application of Ser. No. 398,272, filed on Sept. 17, 1973 now abandoned and which claims the priority of German Pat. application P 22 46 433.1, filed on Sept. 21, 1972.

The present invention concerns the use of 3-aminopropionic acid derivatives disubstituted at the nitrogen atom as active ingredients having insect repellant activity, in particular in the form of cosmetic or technical preparations as new insect repellants.

Unlike insecticides, which do not prevent insects from settling or from stinging with the possibly resulting infection as their effect begins only after a certain latency period, insect repellants prevent harmful insects from flying in or touching and from stinging and sucking on surfaces attractive to them, as for instance the skin of animals and humans, which has previously been treated with these agents. In many areas, the driving off of stinging, blood-sucking and other bothersome insects is an urgent need, because they do not only molest people and domestic animals but may in part also transmit diseases. Active substances for driving off such insects, therefore, have an important sanitary, hygienic and cosmetic function to fulfill.

For the purpose of repelling harmful insects from surfaces attractive to them, numerous active substances have already been proposed. Especially well known and in use for some time are dimethylphthalate and m-toluylic acid-N,N-diethylamide (DEET). These compounds have attained considerable importance as effective insect repellants. The known commercial insect repellants are not based on a common principle of constitution.

An essential disadvantage of known insect repellants consists in their property of damaging plastic objects of daily use by partially dissolving or swelling the plastic. Besides, many of the known insect repellants do not possess or do so only in limited measure- the high skin and mucous membrane tolerance necessary and desirable for their cosmetic use.

It was, therefore, an object of the invention to develop and discover new insect repelling agents which, besides being unexpectedly improved repellants, have an excellent tolerance for the human skin, in particular the mucosa, and do not attack or damage plastic objects even after prolonged contact time.

It was found that certain 3-aminopropionic acid derivatives (beta-alanine derivatives) disubstituted at the nitrogen atom exhibit a markedly improved, long-lasting insect-repelling action, possess a high skin and mucosa tolerance superior to the known commercial preparations, and moreover have the property of not attacking or damaging plastic objects.

It was surprising to find a strongly marked insect-repelling action among the derivatives of 3-aminopropionic acid substituted at the nitrogen atom especially for the reason that the isomeric 2-aminopropionic acid had been described already several years ago as an insect-attracting substance (attracting especially mosquitoes (A. W. A. Brown, A. G. Charmichael, J. Econ. Entomol. 44, p. 317 (1961); B. Schaerffenberg, E. Kupka: Naturwissenschaften 46, p. 457 (1959)). Hence, the 2-amino compound exhibits a biological effect directly opposite to the effects of the 3-amino compounds of the present invention.

The subject matter of the invention thus are insect-repelling agents for cosmetic or technical purposes, characterized by containing an effective amount of at least one 3-aminopropionic acid derivative disubstituted at the nitrogen atom of the general formula I

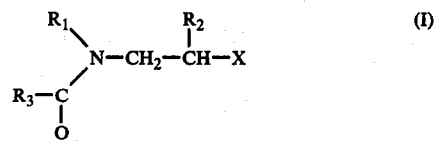

$R_1$ stands for an unbranched or branched alkyl radical with 1 to 6 carbon atoms, $R_2$ represents a hydrogen atom or a methyl or ethyl group, $R_3$ is an unbranched or branched alkyl or alkoxy group having 1 to 8 carbon atoms, and X stands for —C≡N or for —COOR$_4$, $R_4$ being an unbranched or branched alkyl radical with 1 to 6 carbon atoms.

The substances to be used in accordance with the invention are unambiguously characterized by the above formula (I).

The insect-repelling agents according to the invention, which - usually in addition to common additives and/or vehicles - contain at least one of the stated 3-aminopropionic acid derivatives disubstituted at the nitrogen atom of formula I, constitute a valuable enrichment of the art. This is evident from the results of comparative tests that have been made with a substance according to the invention, 3-(N-n-butyl-N-acetyl)-aminopropionic ethyl ester, in comparison with the known, effective commercial preparations dimethyl phthalate and m-toluylic acid-N,N-diethylamide (DEET), and from which the superiority of the substrate according to the invention over the comparison substances is clearly evident.

A$_1$. TESTING THE INSECT-REPELLENT EFFECT ON AEDES AEGYPTI L. (MOSQUITOES)

Method: The lower arm of a test person served as a mosquito attracting source. It was treated by uniform rubbing with a 5% (by weight) solution of 3-(N-n-butyl-N-acetyl)-aminopropionic ethyl ester in ethanol. The test person's hand was protected by a glove. The lower arm treated with active substance was introduced in a test cage filled with 500 hungry female mosquitoes.

Result: During the planned test period of 5 minutes neither approaches nor bites were observed on the treated lower arm.

To determine the long-term effect of the active substance 3-(N-n-butyl-N-acetyl) aminopropionic ethyl ester, the described test was repeated at intervals of one hour. To compare the effectiveness, the known effective insect repellent substances dimethyl phthalate and m-toluylic acid-N,N-diethylamide were tested in the same manner. Besides 3-(N-n-butyl-N-acetyl)-aminopropionic ethyl ester, 3-(N-ethyl-N-n-butyryl)-aminopropionic methyl ester was also included in the test as a further demonstration of the effectiveness of the present invention.

The results are recorded in the following table:

TABLE 1

| Active Substance | Effect after hours | | |
|---|---|---|---|
| | 1 | 3 | 5 |
| 3-(N-n-butyl-N-acetyl)-aminopropionic ethyl ester | +++ | +++ | +++ |

TABLE 1-continued

| Active Substance | Effect after hours | | |
|---|---|---|---|
| | 1 | 3 | 5 |
| 3-(N-ethyl-N-n-butyryl)-aminopropionic methyl ester | +++ | +++ | +++ |
| m-Toluylic acid-N,N-diethylamide | +++ | +++ | +++ |
| Dimethyl phthalate | +++ | ++ | − |

+++ = complete mosquito protection
++ = partial mosquito protection: many approaches but no bites
− = no mosquito protection: numerous bites

SUMMARY (1) When dimethyl phthalate was used, the effectiveness clearly decreased after 3 hours, after that time (cf. 5-hour value) numerous mosquito approaches and bites were observed on the treated lower arm.

(2) When 3-(N-n-butyl-N-acetyl)-aminopropionic ethyl ester, 3-(N-ethyl-N-n-butyryl)- aminopropionic methyl ester, and m-toluylic acid-N,N-diethylamide were used (i.e. compounds of the present invention), no decrease of the effectiveness was observed even after 5 hours.

A₂. TESTING THE INSECT-REPELLING EFFECT (REPELLENT ACTION) ON ANOPHELES ALBIMANUS (MOSQUITO)

Method: same as in $A_1$, above, except the compounds tested were those in Table 2.

Result: Within the planned test period of 5 minutes, neither approaches nor bites were observed on the lower arm treated with the active substances of the present invention listed in Table 2.

Tests of the long-term effect using dimethyl phthalate and n-toluylic acid-N,N-diethylamide as comparison substances are illustrated in Table 2.

TABLE 2

| Active substance | Effect after hours | |
|---|---|---|
| | 1 | 3 |
| 3-(N-n-butyl-N-acetyl)-aminopropionic ethyl ester | +++ | +++ |
| 3-(N-methyl-N-acetyl)-aminopropionic acid n-butyl ester | +++ | +++ |
| 3-(N-ethyl-N-n-butyryl)-aminopropionic methyl ester | +++ | ++ |
| 3-(N-n-propyl-N-propionyl)-aminopropionic methyl ester | +++ | ++ |
| 3-(N-ethyl-N-carbomethoxy)-aminopropionic ethyl ester | +++ | +++ |
| 3-(N-ethyl-N-carboethoxy)-aminopropionic acid ethyl ester | +++ | +++ |
| m-Toluylic acid-N,N-diethylamide | +++ | − |
| Dimethyl phthalate | − | − |

+++ = Complete mosquito protection
++ = Partial mosquito protection : sporadic approaches, not bites
− = No mosquito protection : numerous bites In view of the great difficulty in warding off Anopheles mosquitoes with repellants (Aedes aegypti mosquitoes can generally be controlled by repellants much more easily), the superiority of the substances of the invention appearing from the table over the known commercial preparations is of particular importance.

B. TEST FOR MUCOSA TOLERANCE

Test object: Rabbit eye p Method: 1 drop of the active substance to be tested was dropped into the conjunctival sac (tear sac) of one rabbit eye. The rabbit's other eye (control side) was treated in the same manner with 1 drop of physiologic salt solution. After a contact time of 1 minute, the treated eyes were rinsed with lukewarm water. Evaluations of reddening effect on the rabbit's eyes were made after 1, 3, 5, 24, 48 and 96 hours.

In this test series were included, besides a compound of the present invention, 3-(N-n-butyl-N-acetyl)-aminopropionic ethyl ester, as comparison substances, dimethyl phthalate and m-toluylic acid-N-N-diethylamide.

The result appears from the following table:

TABLE 3

| Active substance | Checkup after hours | | | | |
|---|---|---|---|---|---|
| | 1 | 3 | 24 | 48 | 90 |
| 3-(N-n-butyl)-N-acetyl)-aminopropionic ethyl ester | + | + | + | − | − |
| m-Toluylic acid-n,N-diethylamide | ++ | ++ | ++ | + | − |
| Dimethyl phthalate | ++ | ++ | ++ | + | − |

++ = intense reddening
+ = slight reddening
− = negative

C. TESTING THE EFFECT ON PLASTIC OBJECTS (PARTIAL DISSOLVING OR SWELLING)

Method: A ball point pen of plastic and a 10 × 10 cm piece of plastic raincoat (slicker) of soft PVC were placed for 6 hours in the diluted active substance 3-(N-n-butyl-N-acetyl)-aminopropionic ethyl ester of the invention (30 vol.% in ethanol). As comparison substance there were used - in the same dilution - dimethyl phthalate and m-toluylic acid-N,N-diethylamide.

RESULT:

(1) When 3-(N-n-butyl-N-acetyl)-aminopropionic ethyl ester was used, the two plastic objects showed no change of constitution.

(2) By the comparison substances M-toluylic acid-N,N-diethylamide and dimethyl phthalate both plastic objects were attacked: their surfaces were rough, tacky and swollen.

The 3-aminopropionic acid derivatives disubstituted at the nitrogen atom (formula I) according to the invention are in part known substances, in part not yet described in the literature. They can be produced by methods known in themselves. For example, by addition of amines of the formula II

$$R_1 - NH_2 \quad \text{(II)}$$

to the reactive C═C double bond of acrylic acid derivatives (or 2-alkylacrylic acid derivatives) of the formula III

$$H_2C=C-X \quad \text{(III)}$$
$$\quad \ \ |$$
$$\quad \ \ R_2$$

where $R_1$ in formula II, and $R_2$ and X in formula III have the meanings stated above (formula I).

The reaction of the amines of formula II with the acrylic acid derivatives of formula III - possibly substituted in 2-position by an alkyl radical - can occur in the presence or the absence of diluents, such as alcohols, aliphatic or aromatic hydrocarbons, it being necessary, in order to avoid the formation of 2:1 adducts of the formula V:

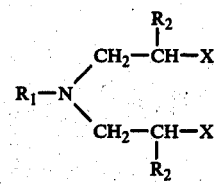

to choose a molar ratio of 2:1 between the amine (II) and the acrylic acid derivative (III).

This addition reaction, which leads to the intermediate compounds of the formula IV,

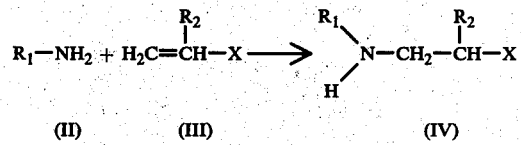

that is, to the 3-aminopropionic acid derivatives monosubstituted at the nitrogen atom, is carried out advantageously at temperatures between 0° and 100° C., preferably in the temperature range between 5° and 30° C.

The reaction can be carried out at normal pressure, respectively with the use of amines very volatile at room temperature and also, to accelerate the reaction, at elevated pressure. The isolation and working up of the reaction products according to formula IV is done in the usual manner by distillation.

The preparation of the end products, of the 3-aminopropionic acid derivatives disubstituted at the nitrogen atom according to formula I, from the intermediate products according to formula IV occurs in a subsequent reaction step by conversion of the adducts of formula IV with reactive carboxylic acid chlorides of formula IV or with chloroformic acid esters of formula VII in a manner known in itself:

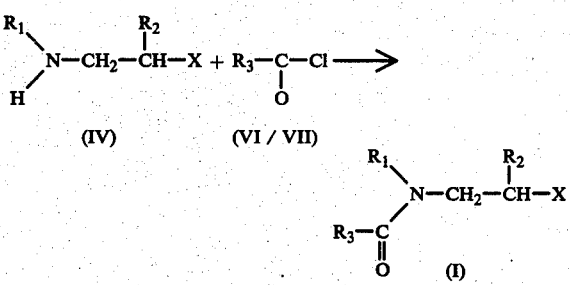

where $R_3$ in formulas VI and VII has the meaning indicated above (formula I).

This conversion is advantageously carried out in the presence of tertiary nitrogen bases, such as triethylamine or pyridine, at temperatures between 0° and 30° C., advantageously with the use of diluents. Aromatic and aliphatic hydrocarbons have proved to be suitable diluents for this purpose. The reaction products (end products) obtainable by the conversion and corresponding to formula I can be isolated and purified in the usual manner by distillation.

Examples of 3-aminopropionic acid derivatives disubstituted at the nitrogen atom obtainable by the described process and usable as insect repellants according to the present invention are:

3-(N-n-butyl-N-acetyl)-aminopropionic ethyl ester B.P.$_{0.5}$:126°–127° C.

3-(N-n-butyl-N-n-butyryl)-aminopropionic acid nitrile B.P.$_{0.3}$:135°–140° C.

3-(N-ethyl-N-n-butyryl)-aminopropionic methyl ester B.P.$_3$:122°–125° C.

3-(N-ethyl-N-acetyl)-aminopropionic ethyl ester B.P.$_{0.6}$:105°–106° C.

3-(N-n-propyl-N-acetyl)-aminopropionic ethyl ester B.P.$_{0.3}$:101°–102° C.

3-(N-methyl-N-acetyl)aminopropionic n-butyl ester B.P.$_{0.15}$:112°–116° C.

3-(N-n-propyl-N-n-propionyl)-aminopropionic methyl ester B.P.$_3$:135°–138° C.

3-(N-n-butyl-N-acetyl)-aminopropionic n-butyl ester B.P.$_{0.3}$:136°–138° C.

3-(n-ethyl-N-acetyl)-amino-2-methylpropionic ethyl ester B.P.$_3$:118°–120° C.

3-(N-ethyl-N-propionyl)-amino 2-methyl propionic ethyl ester B.P.$_3$;123°–126° C.

3-(N-ethyl-N-carbomethoxy)-aminopropionic ethyl ester B.P.$_3$:95°–98° C.

3-(N-ethyl-N-carbethoxy)-aminopropionic ethyl ester B.P.$_5$:118°–120° C.

3-[N-methyl-N(2-ethyl-hexanoyl)]-aminopropionic methyl ester B.P.$_{0.05}$:106°–108° C.

The active substances according to the invention, while having little toxicity for warm-blooded animals, show a strong insect-repelling effect (repellent action) against blood-sucking insects. As the effect persists for a long time, these agents can advantageously be used in the form of preparation suitable for this purpose to ward off harmful blood-sucking insects. These agents are especially well suited for the repulsion of mosquitoes.

The active substances of the invention, which can be used undiluted or preferably diluted, can be incorporated in the forms of presentation common for repellants and be used in all forms of use common in cosmetics, for example in the form of solutions, emulsions, ointments, creams, powders, pastes, sticks or sprays, or as aerosols from spray cans.

These preparations are produced in known manner by mixing or diluting the active substances with solvents, additives and/or vehicles, possibly with the use of emulsifiers.

The active substances according to the invention may be present in the preparations as mixture constituent, and possibly also in mixture with other active substances, such as sun protectants.

The preparations generally contain 0.1 to 95% by weight of the active substance or substances, more particularly between 0.5 and 90% by weight. Preferably, however, the active substance proportion in the preparations should be 5 to 20% by weight.

For protection against harmful blood-sucking insects the active substances of the invention can be applied undiluted or diluted in the form of their preparations by rubbing in or spraying on the human or animal skin. A particularly good effectiveness is obtained when they are used in the form of alcoholic-aqueous lotions. The active substances of the invention are suitable also for addition to impregnating agents for textile webs, garments and packing materials, and as components of polishing, cleansing and window-cleaning agents.

The following examples for preparations using the active substances according to the invention serve for the further elucidation of the invention.

EXAMPLE 1

5 g 3-(N-n-butyl-N-acetyl)-aminopropionic acid n-butyl ester 5 g trioctanoin (esterification product between glycerin and 3 moles of octane carboxylic acid)

5 g 2-octyl-dodecanol 50 g isopropanol 10 g water are mixed. The solution thus obtained is suitable, besides as a lotion, especially as sprayable insect repellant.

EXAMPLE 2

48 g of a colloid-disperse mixture of 90 parts cetyl-stearyl alcohol and 10 parts sodium cetyl-stearyl sulfate ("Lanette N", Deutsche hydrierwerke, Dusseldorf)

24 g cetyl alcohol 24 g mineral oil (viscosity about 3° Engler/50° C.)

20 g 3-(N-n-butyl-N-acetyl)-aminopropionic ethyl ester are mixed and the mixture obtained is heated to 70° C. A mixture of 240 g water and 40 g glycerin prepared separately therefrom and likewise heated to 70° C. is added to the first named mixture at elevated temperature (about 70° C.) while stirring. With continuous stirring there is formed upon cooling a cream which is suitable as insect repellant for rubbing into the skin.

What is claimed is:

1. A method of repelling insects comprising applying to a region from which the insects are to be repelled a repellent composition consisting essentially of a diluent and 0.1 to 95% by weight of at least one active repellent substance having the structure

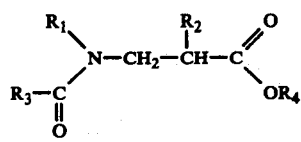

in which $R_1$ is a branched or unbranched alkyl radical having 1 to 6 carbon atoms, $R_2$ is a hydrogen atom or a methyl group or ethyl group;

$R_3$ is a branched or unbranched alkyl or alkoxy group having 1 to 8 carbon atoms, and $R_4$ is a branched or unbranched alkyl radical having 1 to 6 carbon atoms.

2. The method according to claim 1 in which the repellent active substance is present in an amount of 5 to 20% by weight.

3. The method according to claim 1 wherein $R_2$ is hydrogen or methyl and $R_3$ is a branched or unbranched alkyl group having 1 to 8 carbon atoms or a methoxy or ethoxy group.

4. The method according to claim 1 in which the repellent active substance is 3-(N-n-butyl-N-acetyl)-amino propionic ethyl ester.

5. The method according to claim 1 in which the diluent is inert to human and animal skin.

6. The method according to claim 5 in which the inert diluent is a solvent.

* * * * *

UNITED STATES PATENT OFFICE
CERTIFICATE OF CORRECTION

PATENT NO. : 4,127,672
DATED : November 28th, 1978
INVENTOR(S) : MANFRED KLIER, et al It is certified that error appears in the above-identified patent and that said Letters Patent are hereby corrected as shown below:

Column 1, line 61, cancel "Charmichael" insert -- Carmichael --

Column 2, line 5, cancel

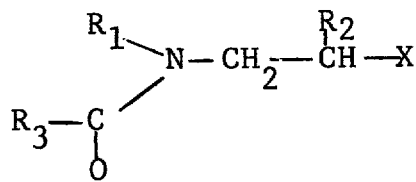

Insert

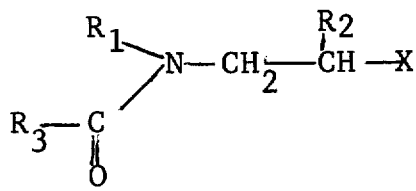

Column 4, Table 3, before line 10, cancel "m-Toluylic acid-n"

insert -- m-Toluylic acid-N --

Column 4, line 32, cancel "M-toluylic acid-" insert -- m-toluylic acid- --

Column 4, between lines 55 and 60, formula II, cancel "$R_1$—NH2" insert -- $R_1$—$NH_2$ --

UNITED STATES PATENT AND TRADEMARK OFFICE
CERTIFICATE OF CORRECTION

PATENT NO. : 4,127,672
DATED : November 28th, 1978
INVENTOR(S) : MANFRED KLIER, et al It is certified that error appears in the above-identified patent and that said Letters Patent are hereby corrected as shown below:

Column 5, between lines 20 and 30, cancel

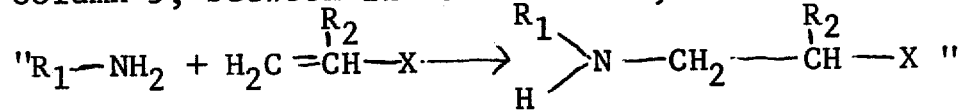

insert --
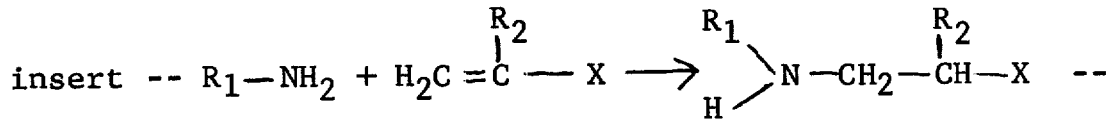
--

Column 5, between lines 46 and 53, cancel

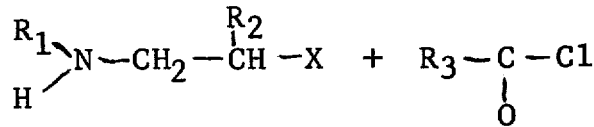

UNITED STATES PATENT AND TRADEMARK OFFICE
CERTIFICATE OF CORRECTION

PATENT NO. : 4,127,672  
DATED : November 28th, 1978  
INVENTOR(S) : MANFRED KLIER, et al Page 3 of 3

It is certified that error appears in the above-identified patent and that said Letters Patent are hereby corrected as shown below:

insert

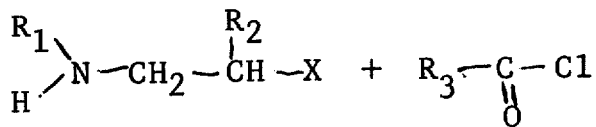

Column 7, line 21, cancel "hydrierwerke," insert

-- Hydrierwerke --

Signed and Sealed this

Seventeenth Day of April 1979

[SEAL]

Attest:

RUTH C. MASON  
Attesting Officer

DONALD W. BANNER  
Commissioner of Patents and Trademarks